United States Patent
Ranganathan et al.

(10) Patent No.: US 10,076,673 B2
(45) Date of Patent: Sep. 18, 2018

(54) INTERACTIVE DOSE GRADIENT BASED OPTIMIZATION TECHNIQUE TO CONTROL IMRT DELIVERY COMPLEXITY

(71) Applicant: KONINKLIJKE PHILIPS N.V., Eindhoven (NL)

(72) Inventors: Vaitheeswaran Ranganathan, Bangalore (IN); Gipson Joe Anto, Kaliyal (IN); Prashant Kumar, Bangalore (IN); Sivaramakrishnan Krishnaiyer Raman, Bangalore (IN); Deepak Uddhavrao Mahajan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 173 days.

(21) Appl. No.: 14/785,751

(22) PCT Filed: Apr. 17, 2014

(86) PCT No.: PCT/IB2014/060785
§ 371 (c)(1),
(2) Date: Oct. 20, 2015

(87) PCT Pub. No.: WO2014/181204
PCT Pub. Date: Nov. 13, 2014

(65) Prior Publication Data
US 2016/0089549 A1    Mar. 31, 2016

Related U.S. Application Data

(60) Provisional application No. 61/819,886, filed on May 6, 2013.

(51) Int. Cl.
*A61N 5/10* (2006.01)

(52) U.S. Cl.
CPC ......... *A61N 5/1031* (2013.01); *A61N 5/1036* (2013.01); *A61N 5/1045* (2013.01); *A61N 5/1077* (2013.01); *A61N 2005/1074* (2013.01)

(58) Field of Classification Search
CPC ............... A61N 5/1031; A61N 5/1045; A61N 2005/1074; A61N 5/1077; A61N 5/1036
See application file for complete search history.

(56) References Cited

U.S. PATENT DOCUMENTS 6,504,899 B2    1/2003    Pugachev
6,661,872 B2    12/2003    Bova
(Continued)

FOREIGN PATENT DOCUMENTS

EP    2260902 A1    12/2010
WO    2011053802 A2    5/2011

OTHER PUBLICATIONS

Chang, S. X., et al.; Dose optimization via index-dose gradient minimization; 2002; Med. Phys.; 29(6)1130-1146.
(Continued)

*Primary Examiner* — Christine H Matthews
*Assistant Examiner* — Joshua D Lannu

(57) ABSTRACT

A method for dose-gradient based optimization of an intensity modulated radiation therapy plan. First, an optimizer (6) performs a first optimization (40) of the plan to generate dose distributions corresponding to the plan. Next, the optimizer (6) generates a beam specific dose gradient map (42) for each beam of the plan. Then, new dose gradients are specified (44) for the plan. Last, the optimizer (6) performs a final optimization (46) using the new dose gradients. The final optimization is given the new dose gradients as soft constraints into an objective function. The optimizer (3) applies a limiting factor to the objective function such that a first dose gradient is limited by the optimizer only if the (Continued)

first dose gradient exceeds the new dose gradient for a specific beamlet.

19 Claims, 5 Drawing Sheets

(56) References Cited

U.S. PATENT DOCUMENTS

| | | | |
|---|---|---|---|
| 7,027,557 B2 | 4/2006 | Llacer | |
| 7,162,008 B2 | 1/2007 | Earl et al. | |
| 7,902,530 B1 | 3/2011 | Sahadevan | |
| 2011/0075806 A1* | 3/2011 | Nord | A61N 5/103 378/65 |
| 2011/0122997 A1* | 5/2011 | Lu | A61N 5/1031 378/65 |
| 2012/0136677 A1* | 5/2012 | Ziegenhein | A61N 5/1031 705/2 |
| 2012/0323599 A1 | 12/2012 | Bal | |
| 2013/0102830 A1 | 4/2013 | Otto | |

OTHER PUBLICATIONS

Coselmon, M. M., et al.; Improving IMRT delivery efficiency using intensity limits during inverse planning; 2005; Med. Phys.; 32(5)1234-1245.

Fuss, M., et al.; Intensity-modulated radiosurgery: improving dose gradients and maximum dose using post inverse-optimization interactive dose shaping; 2007; Technology in Cancer Research & Treatment; 6(3)197-204.

Galvin, J. M., et al.; Implementing IMRT in Clinical Practice: A joint Document of the American Society for Therapeutic Radiology and Oncology and the American Association of Physicists in Medicine; 2004; Int. J. Radiation Oncology Biol. Phys.; 58(5)1616-1634.

Hardemark, B., et al.; Direct machine parameter optimization with RayMachine in Pinnacle; 2003; RaySearch Laboratories; 3 pages.

Litzenberg, D. W., et al.; Incorporation of realistic delivery limitations into dynamic MLC treatment delivery; 2002; Med. Phys.; 29(5)810-820.

Markman, J., et al.; Beyond bixels: Generalizing the optimization parameters for intensity modulated radiation therapy; 2002; Med. Phys.; 29(10)2298-2304.

Matuszak, M. M., et al.; Adaptive diffusion smoothing: A diffusion-based method to reduce IMRT field complexity; 2008; Med. Phys.; 35(4)1532-1546.

Mohan, R., et al.; The impact of fluctuations in intensity patterns on the number of monitor units and the quality and accuracy of intensity modulated radiotherapy; 2000; Med. Phys.; 27(6)1226-1237.

Shapard, D. M., et al.; Direct aperture optimization: A turnkey solution for step-and-shoot IMRT; 2002; Med. Phys.; 29(6)1007-1018.

* cited by examiner

INTERACTIVE DOSE GRADIENT BASED OPTIMIZATION TECHNIQUE TO CONTROL IMRT DELIVERY COMPLEXITY

CROSS REFERENCE TO RELATED APPLICATIONS

This application is a national filing of PCT application Serial No. PCT/IB2014/060785, filed Apr. 17, 2014, published as WO 2014/181204 A2 on Nov. 13, 2014, which claims the benefit of U.S. provisional application Ser. No. 61/819,886 filed May 6, 2013, which is incorporated herein by reference.

The present application relates to the medical arts and finds particular application with radiation treatment planning and will be described with particular reference thereto. However, it is to be appreciated that it will also find application in other medical interventions and treatment procedures. When a patient is diagnosed with cancer, several treatment options can be pursued. One treatment option is radiation therapy. When radiation therapy is selected, a detailed plan is constructed from large amounts of data about the patient.

In the past decade, technological advancements have provided a big leap in the field of intensity modulated radiation therapy (IMRT), intensity modulated proton therapy (IMPT) and the like, to improve dose delivery. Recently the research interest has shifted towards methods of automating various tasks involved in plan generation, starting from beam placement to dose optimization, to assist and reduce the workload burden on the clinical user.

Plan evaluation is classified into three phases: 1. Physical evaluation, 2. Technical evaluation and 3. Clinical evaluation. The physical and technical aspects of a plan are generally examined by a technician after the completion of the plan. The clinical aspects of a plan are investigated by a radiation oncologist. Currently an IMRT plan is evaluated based on five categories that cover the physical, technical and clinical aspects of a plan: 1. Geometric analysis, 2. Dose distribution analysis, 3. Dose Volume Histogram (DVH) analysis, 4. Parametric analysis and 5. Deliverability analysis.

The geometric analysis is performed to evaluate the optimality of beams placement. Beam placement is a very important step. The quality of optimization is mainly influenced by the number of beams and their angles. Rules have been formulated for optimal beam placement in IMRT in view of increasing the optimality and deliverability of an IMRT plan.

The dose distribution analysis qualitatively verifies the optimality of dose distribution in axial, coronal and sagittal planes. This analysis can be further split up into 2D analysis and 3D analysis. 2D dose distribution analysis implies the evaluation of dose distribution slice-by-slice. This type of analysis is used to evaluate the conformality of the prescribed dose with respect to the target volume in each slice. This type of analysis can also reveal the distribution of cold or hot spots in and around the target volume. Cold or hot spots are areas within the target and organs at risk that receive less or greater than the intended dose of radiation. The 3D distribution analysis is useful in determining how conformal a dose distribution is to the overall target volume with respect to a set of beam orientations.

Dose Volume Histograms (DVH) are a powerful tool for evaluating the optimality of a plan. A DVH represents a 3-dimensional dose distribution in a graphical 2-dimensional format. A DVH for target volume graphically represents the quality of the dose distribution in terms of coverage, conformity and homogeneity. The DVH curves for Organs-at-risk (OARs) represent the efficiency at which the OARs are spared in terms of mean and maximum dose.

The parametric analysis is performed to quantitatively verify the optimality of dose. The parameters used in this analysis are: (a) minimum, mean and maximum dose for target volume and OARs and (b) coverage, conformity and homogeneity indices for target volume. Apart from physical metrics for plan evaluation, a plurality of biological metrics are used in plan evaluation. These biological metrics include Equivalent Uniform Dose (EUD), Tumor Control Probability (TCP) and Normal Tissue Complication Probability (NTCP) and the like.

Deliverability analysis is performed in order to evaluate how robust the plan is in terms of dose delivery. This analysis involves the verification of parameters such as number of segments, minimum or average monitor units (MU) per segment, Minimum Segment Area (MSA), total delivery time and the like. MU is a measure of machine output of a linear accelerator in radiation therapy. The deliverability analysis reveals whether a plan is actually deliverable or not.

Radiation treatment plan (RTP) evaluation is a time consuming process which also requires expertise. The inverse planning methodology used in IMRT is a complex process that is potentially susceptible to noise and high frequency spatial fluctuations that produce sharp fluence peaks and valleys, e.g. gradients. These features are considered desirable when they help achieve the objectives given to the treatment planning system. However, these features can lead to undesirable effects, including large increases in monitor units (MU), sensitive to geometric uncertainties, and prolonged delivery times. The resulting MU is directly proportional to the frequency and amplitude of fluctuations in the intensity distribution of a beam. Another concern is the additional dose delivered to the patient from transmission and leakage due to excessive MU, i.e. "hot" spots. As intensity patterns become more complex, the differences between the computed, sequenced, and delivered intensity patterns increase.

Methods were developed to attempt to increase the efficiency of IMRT process by reducing unnecessary modulation in delivered IMRT beams. One approach to solve this problem was incorporating smoothing algorithms after optimization that produces more continuous intensity patterns to improve deliverability and reduce excessive MU. However, attempts to reduce beam complexity by smoothing often results in plan degradation because the smoothing algorithm cannot distinguish between areas of desirable and undesirable modulation.

Another approach is accepting that some of the high intensity peaks are not necessary for producing a quality plan. Unnecessary modulation can be avoided by applying "Intensity Limits" for a plan in the optimization process. Such beamlet intensity restriction approaches are not accurate because it is difficult to determine a single cut-off intensity level applicable across an entire DVH plan. Aperture-based IMRT techniques such as direct aperture optimization (DAO) and direct machine parameter optimization (DMPO) help reduce some delivery complexity. However, the direct aperture-based optimization problem is much harder to solve than fluence-based optimization. In aperture-based techniques, a good starting point for optimization is necessary to ensure a high quality plan. The selection of appropriate maximum number of segments is central in direct aperture-based optimization approaches for striking a balance between plan optimality and dose deliverability.

The present application provides an improved dose gradient-based optimization technique to control IMRT delivery complexity.

In accordance with one preferred method of the present application, a method for optimizing an intensity modulated radiation therapy plan is provided, comprising: optimizing the plan according to initial plan specified settings to create optimized dose distributions in beam's eye view; generating dose gradient maps from the optimized does distributions in beam's eye view; and specifying new dose gradients for user specified regions in beam's eye view.

In accordance with one preferred embodiment of the present application, a treatment plan optimization system is provided, comprising a user interface to receive an input from a user; a non-transitory memory module for storing a treatment plan data set comprising data from multiple sources; and an optimizer. The optimizer is programmed to optimize the plan according to initial plan specified settings to create optimized dose distributions in beam's eye view; generate dose gradient maps from the optimized does distributions in beam's eye view; and specify new dose gradients for user specified regions in beam's eye view.

In accordance with another method of the present application, a dose-gradient based optimization method is provided, comprising optimizing the plan according to initial plan specified settings to create optimized dose distributions for a beam's eye view; dividing the dose distributions into a plurality of beamlets; calculating a first dose gradient value for each beamlet of the plurality of beamlets; compiling dose gradient maps from the dose gradient values of each beamlet; determining insufficient dose gradients within the dose gradient maps of each beam's eye view; delineating sub-regions within the dose gradient maps with respect to the insufficient dose gradients; specifying user dose gradients for the delineated sub-regions; and performing a second optimization using the user dose gradients.

One advantage resides in that calibration time and cost are reduced.

Another advantage is increased predictability of possible changes in plan quality after optimization.

One further advantage is easier identification of over-modulated beamlets.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 4:
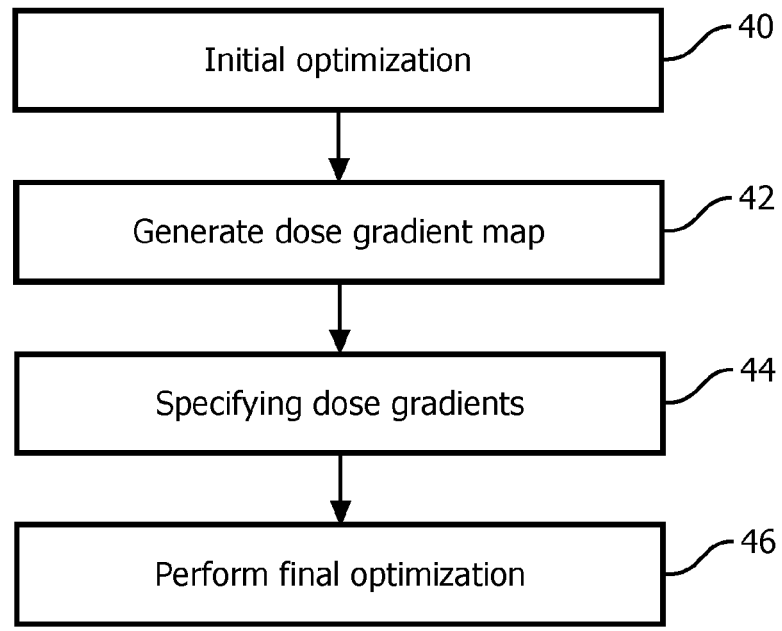
Figure 5:
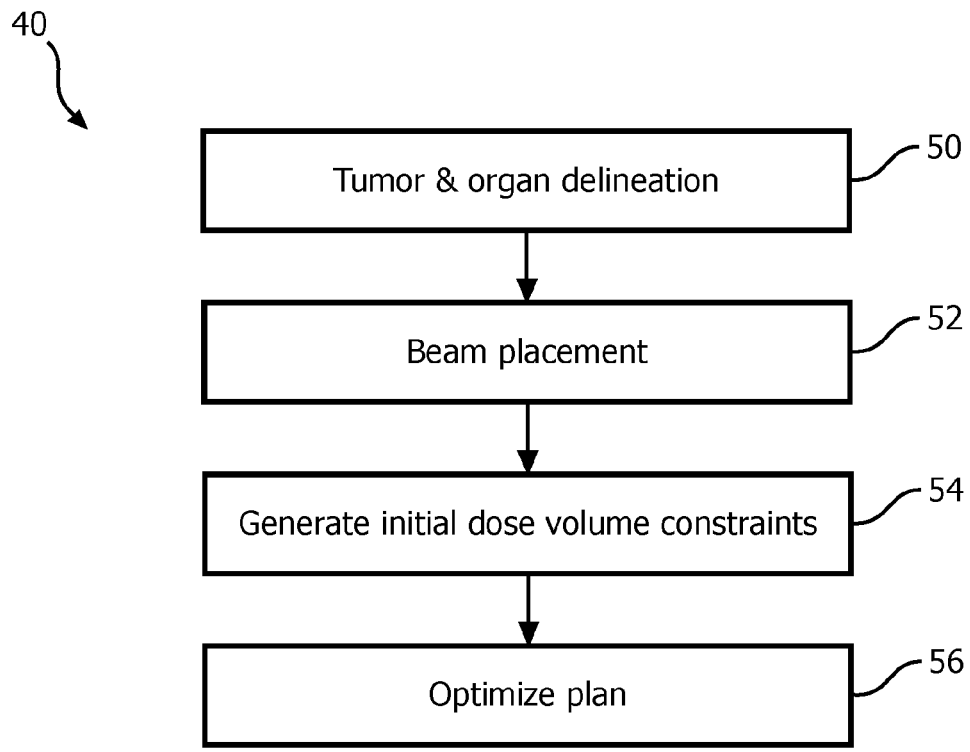
Figure 6:
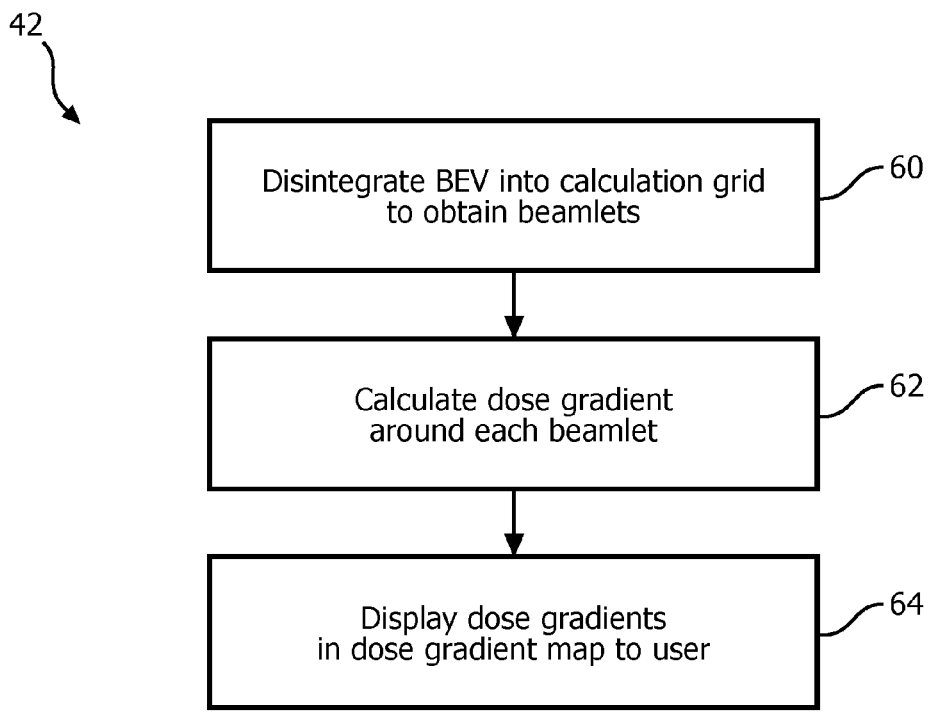
Figure 7:
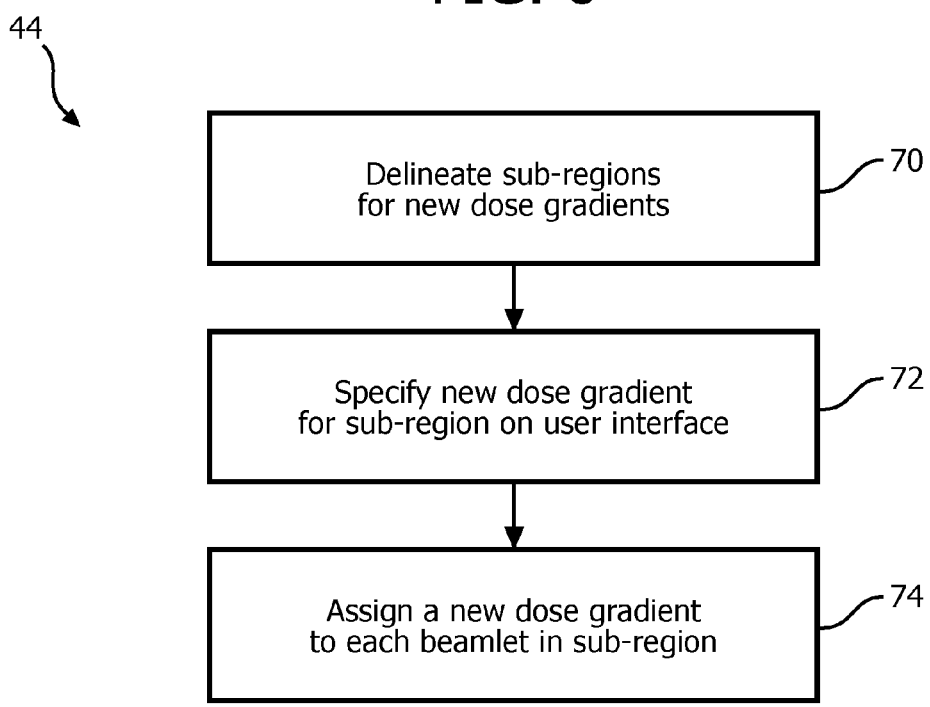

FIG. 4 depicts a method for dose-gradient optimization.
FIG. 5 depicts a method for initially optimizing a plan.
FIG. 6 depicts a method for generating dose gradients.
FIG. 7 depicts a method for specifying new dose gradients.

The present application provides functionality to optimize an IMRT plan using dose-gradient based optimization. The application provides functionality to store and access treatment plan data specific to a patient, where the data is comprised of multiple distributed sources. The present application provides functionality to perform an initial optimization of the treatment plan. The application provides functionality to generate dose gradient maps based on the treatment plan data. The application provides functionality to specify dose gradients for specific regions in beam's eye view and for a single beam out of multiple beams used in the plan. The application provides further functionality to perform a final optimization on the plan. The application provides functionality to accept user input and display results in real time to the user for plan manipulation.

Figure 1:
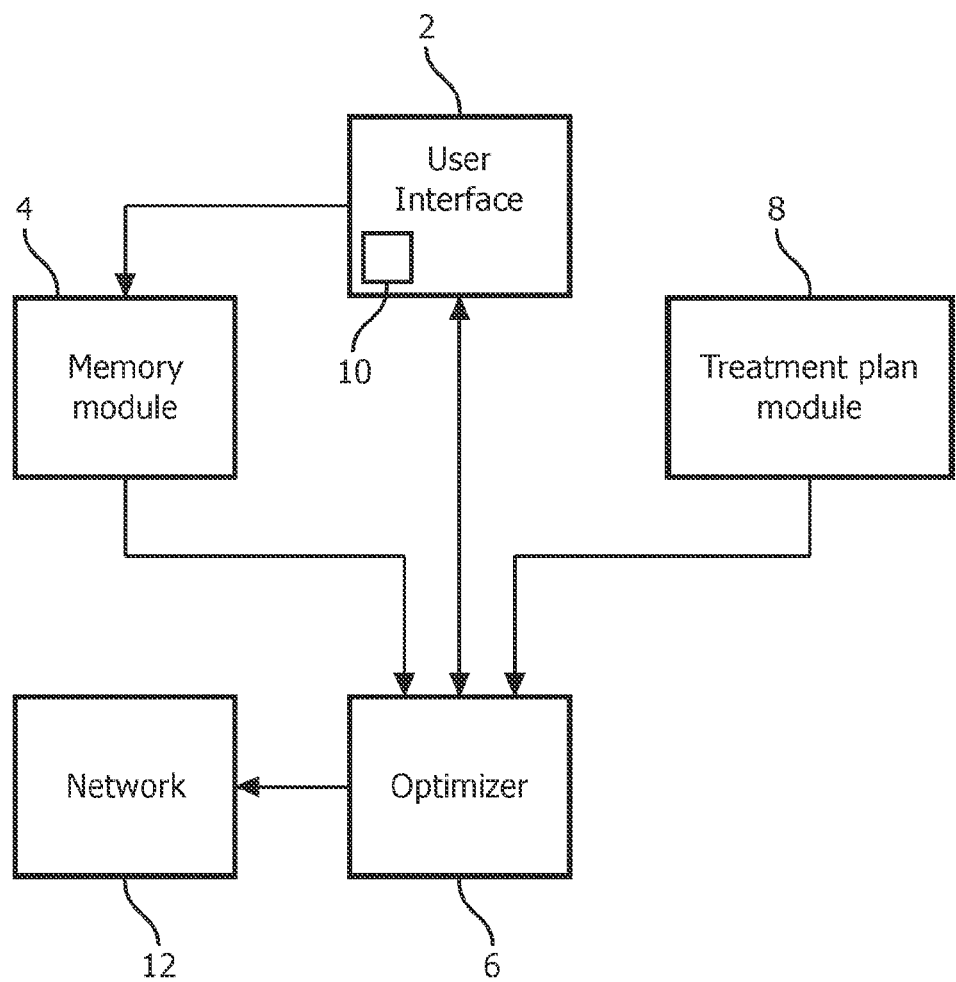
FIG. 1 depicts an embodiment of a radiation therapy plan evaluation system.

The dose gradient is directly proportional to the intensity modulation such that modifying the gradient likewise modifies the intensity modulation of a dose. FIG. 1 depicts an embodiment of a system for providing dose gradient-based optimization to control treatment plan delivery complexity. The optimization system includes a user interface 2 which accepts input from the user. The user interface 2 accepts user input through a mouse, keyboard, touchscreen, display, microphone, data file, and the like. The user is generally an oncologist or technician with knowledge of the plan and the patient status. A memory module 4 includes a non-transitory computer readable medium which stores data and inputs. The memory module 4 accepts inputs from the user interface 2 and stores the inputs as data that is accessed by an optimizer 6. The optimizer 6 includes one or more processors for accessing and processing data. The optimizer 6, in one embodiment, includes non-transitory computer readable media for storing instructions for the one or more processors.

Figure 2:
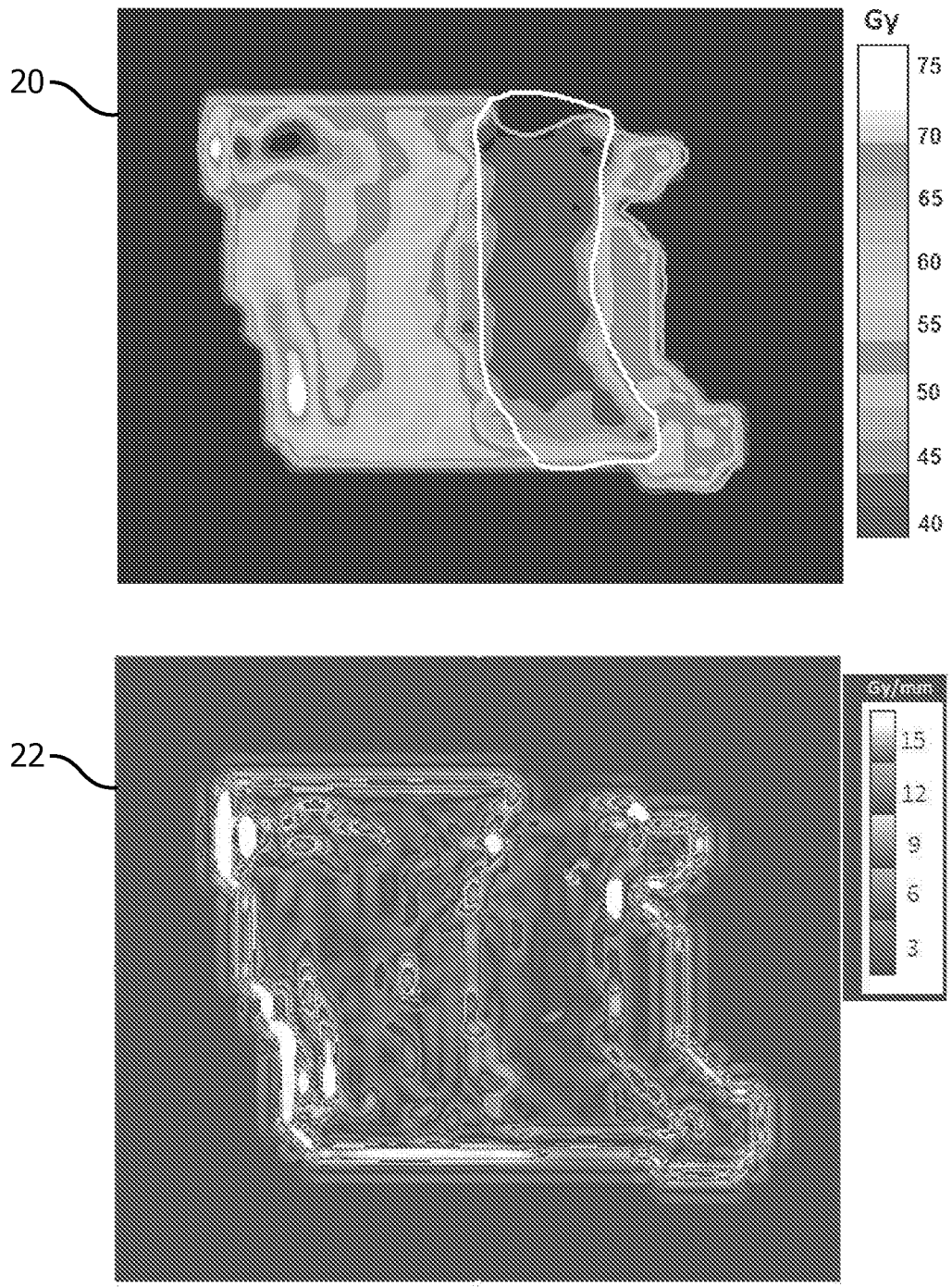
FIG. 2 depicts a dose distribution map (upper) and a derived corresponding dose gradient map (lower) based on the dose distribution map.

The optimizer 6 is connected to the rest of the modules in the system. The optimizer 6 accesses a treatment plan residing at a treatment plan module 8 and accesses data needed for optimization. The optimizer 6 is connected to a display 10. The display 10 is an LCD, TFT, LED, CRT, touchscreen, or another screen implementation. In some embodiments, the display 10 is located within the user interface 2. For example, with reference to FIG. 2, the display 10 displays to a user a view of a dose distribution (FIG. 2, upper) and a corresponding dose gradient map (FIG. 2, lower). The user utilizes the user interface 2 to alter the doses by changed dose gradients on the map. In one embodiment, the user interface 2 accepts the user input via a pen, stylus, or other marking tool.

The optimizer 6 is also connected wired or wirelessly to a network 12 over which the optimized plan can be distributed to other doctors or treatment providers for further review. For example, the plan is distributed over the network 12 to the oncologist who displays and reviews the plan in his/her office and sends approval, comments, corrections, and etc. back over the network 12.

As part of the treatment plan, a technician or clinician typically prescribes a large dose to target volume and smaller maximum doses to surrounding normal tissues/organs as needed to achieve the prescribed dose distribution. The technician places a required number of beams in appropriate gantry angles. The optimizer 6 performs an initial optimization of the plan located on the treatment plan module 8. The initial optimization initializes the details of the plan. An initial optimization sequence is performed as either a fluence based optimization or aperture based optimization. The optimizer 6 calculates the dose and generates dose distributions in beam's eye view for display on the display 10 to the user. For a chosen beam angle, the optimizer 6 retrieves the optimized dose distribution in an isocenter plane, i.e. a plane orthogonal to the beam and intersecting the isocenter, for each beam in beam's eye view. That is the viewer views the dose distribution as if looking from the beam source along the beam.

From the generated dose distributions, the optimizer 6 converts the dose distributions into dose gradient maps. The dose gradient maps are beam specific views of the rate of dose change at the isocenter plane. The dose gradient maps are displayed to the user on the display 10 in beam's eye view. The optimizer 6 shows beam-specific views for a particular beam, and switches off dose contributions of the other beams to the isocenter plane. This allows the user to easily relate the dose gradient map to the intensity modulation of that particular beam.

The optimizer 6 converts the dose distributions to dose gradient maps by first disintegrating a given beam's eye view (BEV) into a calculation grid comprising a plurality of grid points, i.e. beamlets. The dose distribution obtained in the initial optimization is displayed on the display 10 through the BEV of each beam accounting for the stipulated BEV grid resolution. The optimizer 6 converts the BEV-specific dose distribution into a dose gradient map by computing the dose gradient around each particular beamlet in the calculation grid.

To calculate the dose gradient for a given dose distribution in the BEV, the dose difference is calculated between each beamlet i and its nearest neighbor j on the calculation grid. The gradient $G_i$ at each beamlet i is then calculated as:

$$G_i = \sqrt{\sum \left(\frac{\Delta d_{ij}}{\Delta x_{ij}}\right)^2}$$

Where $G_i$ is the dose gradient at a beamlet i, $\Delta d_{ij}$ is the difference in dose between beamlet i and each of its nearest neighbors j, and $\Delta x_{ij}$ is the distance between the beamlet i and each of the nearest neighbor points j used in the calculation. The optimizer 6 selects four to six neighboring points for gradient calculation in BEV of each beam. The dose gradient is a positive scalar quantity and describes the magnitude of the variations, not the directional behavior of the local gradients. The dose gradient is in dose units per millimeter. With reference to FIG. 2, the dose distribution 20 is displayed next to its corresponding dose gradient map 22. In one embodiment, the dose distribution 20 and the dose gradient map 22 are shown on the display 10 juxtaposed to each other. In another embodiment, the views are shown separately on the display 10.

The optimizer 6 displays the dose gradient maps 22 to the user on the display 10 of the user interface 2. The dose gradient maps can then be manipulated by the user using the user interface 2. For dose gradients, the degree of intensity modulation in a region is directly proportional to the level of dose gradient obtained in the region. The intensity of dose distributed to the region changes by changing the dose gradient.

In one embodiment, the user interface 2 displays the dose gradient maps to the user on the display 10. Since, the dose distributed is directly proportional to the dose gradient, the user can use the user interface 2 to alter the dose gradients to obtain a better dose distribution. The user delineates a BEV-sub-region in the dose gradient map and specifies a chosen dose gradient level for that region. The region relates to the particular set of beamlets that are directed towards the delineated region. The user interface 2, through the display 10, shows outlines of a tumor or organ at risk within or superimposed on the dose gradient map to further aid the user in delineating regions for a specified dose gradient. The user easily relates the anatomy to the dose gradients to further optimize the plan. The outlines are generated by segmenting a 3D diagnostic planning image, e.g. CT, MRI, or the like, and overlaying the segmentation boundaries on the dose map. The dose gradient based fine-tuning allows the user to predict possible impact in the final dose distribution after optimization. The dose gradient is measured in dose units per millimeter, which allows the user to directly relate the dose gradient to the anatomy. This enables the user to tune the dose gradient to a required level based on the clinician's prescription for the target volume and surrounding organs at risk. The level of reduction in dose gradient for a particular BEV-sub-region is decided manually by the user based on DVH curves obtained for target volume and other organs. The user specifies the dose gradient within the BEV-sub-region. The optimizer 6 then uses the user input from the user interface 2 to assign dose gradient values to each beamlet within the BEV-sub-region. In one embodiment, the user interface 2 accepts input from editing tools, e.g. pencil, paint brush, stylus and the like, where the user physically delineates or adjusts the BEV-sub-regions using the editing tools.

In another embodiment, the user delineates multiple small BEV-sub-regions within one dose gradient map and then specifies dose gradients for each region. In one further embodiment, the user delineates BEV-sub-regions with a specific beam's corresponding dose gradient map for each beam of the plurality of beams. In another embodiment, the delineation is performed automatically using the optimizer 6 to delineate regions.

The optimizer 6 then performs a final optimization of the plan using the specified dose gradients. The optimizer 6 uses the specified dose gradients as the maximum allowable dose gradient for the beamlets within the delineated BEV-sub-region. The optimizer 6 inputs the specified dose gradients as constraints for the final optimization of the plan. The final optimization is based on a defined objective function F. In one embodiment, the objective function is defined as:

$$F = \sum_n w_n(D_n - P_n)^2 + \sum_k \sum_j \sum_i \left[w_{ijk}(^{specified}G_{ijk} - G_{ijk})^2\right]$$

Where $P_n$ is the prescribed doses for each voxel n while $D_n$ is the dose computed at point n; and $w_n$ is the weight assigned to a voxel inside a particular organ or tissue; i denotes the beamlet number; j denotes the BEV-sub-region number; and k denotes the beam number. $G_{ijk}$ is the current dose gradient obtained at $i^{th}$ beamlet in $j^{th}$ BEV-sub-region in $k^{th}$ beam using the equation from the previous gradient calculation. $^{specified}G_{ijk}$ is the user-specified dose gradient at $i^{th}$ beamlet in $j^{th}$ BEV-sub-region in $k^{th}$ beam. In one embodiment the $^{specified}G_{ijk}$ is specified by the optimizer 6 for the $i^{th}$ beamlet based on the user specified dose gradient for the entire region.

$W_{ijk}$ of the above objective function is a limiting factor determined by:

$W_{ijk}=0$, if $G_{ijk} \leq {}^{specified}G_{ijk}$ $W_{ijk}=1$; if $G_{ijk} > {}^{specified}G_{ijk}$ The limiting factor ensures that only the dose gradients that exceed the specified dose gradient for a particular beamlet are limited through the optimization process.

In one embodiment, the optimizer 6 performs a fluence-based optimization using the above objective function. The optimizer 6 creates optimal fluence profiles from the fluence optimization and converts the fluence profiles into deliverability profiles. In another embodiment, the optimizer 6 performs an aperture-based optimization such as direct machine parameter optimization (DMPO). The optimizer 6 uses the delivery constraints during the fluence optimization of the DMPO process.

Figure 3:
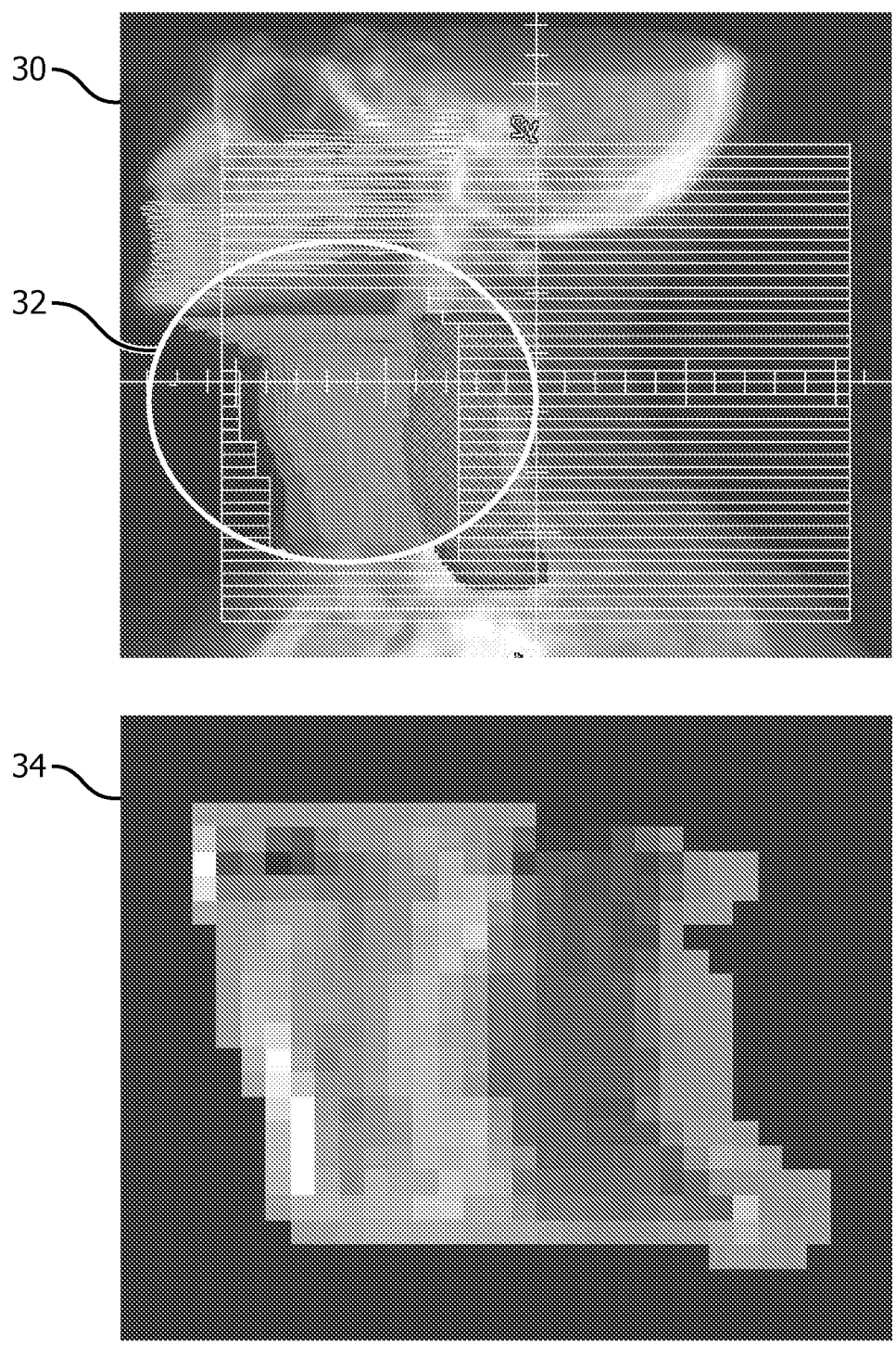
FIG. 3 depicts a beams eye view (upper) for one beam and a corresponding open density matrix (lower) after optimization and conversion.

In one embodiment, the fluence profiles are represented as open density matrices in planning software. With reference to FIG. 3, a beam's eye view of one beam at the isocenter 30 plane is shown (FIG. 3, upper). In the beam's eye view is the target volume 32 indicating the region to be targeted by the beam. Juxtaposed to the beam's eye view (FIG. 3, upper) is the optimized fluence profile 34 (FIG. 3, lower) after the optimizer 6 has performed the final optimization. In one embodiment, the optimizer 6 displays the optimal fluence profile as an open density matrix 34.

With reference to FIG. 4, a method for dose-gradient based optimization is shown. At a step 40, the optimizer 6 performs an initial optimization to obtain the initial plan dose distributions (FIG. 2, upper). At a step 42, dose gradient maps (FIG. 2, lower) are generated by the optimizer 6 from the dose distributions. At a step 44, new dose gradients are specified for regions in the generated dose gradient maps. At a step 46, a final optimization is performed by the optimizer 6 using the specified dose gradients as constraints. The final optimization uses the defined objective function discussed above to obtain optimal fluence profiles and deliverability profiles for the target.

With reference to FIG. 5, the initial optimization step 40 is expanded into multiple steps. At a step 50, a technician delineates the area of a patient's body to be targeted and organs at risk (OARs) to be avoided. Segmentation can be performed to help identify the target and OARs. The technician can be a clinician or radiation oncologist responsible for creating the IMRT plan. At a step 52, the technician determines the proper beam placement for irradiating the target area and minimizing irradiation of the OARs. At a step 54, the optimizer 6 generates initial dose volume constraints based on the plan. The initial dose volume constraints determine how much dose particular areas in and around the target receive. At a step 56, the optimizer 6 performs an initial optimization of the plan using the initial constraints to generate dose distributions. The initial optimization 56 is a fluence-based or aperture-based optimization.

With reference to FIG. 6, the dose gradient maps generation step 42 is expanded into multiple steps. At a step 60, the optimizer 6 disintegrates the dose distribution from the initial optimization into a calculation grid of beamlets. Each beamlet is a grid point in the grid whereby the portions of the dose distribution can be divided by individual beamlets. At a step 62, the optimizer 6 calculates a dose gradient value at each beamlet using the above discussed equation. At a step 64, the optimizer 6 displays the dose gradient values in a dose gradient map (FIG. 2, lower) using the display 10.

With reference to FIG. 7, the specifying new dose gradients step 44 is expanded into multiple steps. At a step 70, using the user interface 2, the user views the dose gradient map of a particular beam and delineates BEV-sub-regions determined to need new dose gradients. The user delineates these regions according to a variety of factors such as location of the dose, or determined "hot" or "cold" spots where dose gradient is too high or low for the plan requirements, and the like. At a step 72, the user specifies a new dose gradient for the BEV-sub-region using the user interface. At a step 74, the optimizer uses the specified dose gradients for the BEV-sub-region to assign dose gradients for each beamlet in the BEV-sub-region.

In one embodiment, the specifying step 44 and final optimization step 46 are iterated until the user is satisfied with the dose distribution, the MU and the intensity modulation. If the user is not satisfied, the steps are repeated until the user is satisfied with the optimized plan and meets the required plan goals. Once the user is satisfied, an open density matrix 34 is generated for the target volume 32. The open density matrix 34 is displayed (FIG. 3, lower) on the display 10 for the user to review.

The methods, and system according to the present application are not only applicable to plan optimization of radiation or proton therapy plans, but e.g. as well in other systems or environments which are subject when providing patient care. Other than oncologists, physicists, and other treatment providers, the present application is of particular use as a training tool to train users to evaluate plans, while providing a check on the users in case a part of the plan is overlooked.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. An intensity modulated radiation therapy treatment plan optimization system, comprising:
   a user interface configured to receive an input from a user;
   a non-transitory memory module configured to store an IMRT treatment plan data set;
   a display configured to display information to the user; and
   an optimizer programmed to:
   optimize the IMRT plan according to initial plan specified settings to create optimized dose distributions in a beam's eye view;
   generate dose gradient maps from the optimized dose distributions in the beam's eye view;
   receive specified dose gradients and specified sub-regions from the user through the user interface; and
   generate new dose gradient maps from the received specified dose gradients and the specified sub-regions.

2. The system according to claim 1, wherein the optimizer is further programmed to:
   perform a second optimization using the specified dose gradients.

3. The system according to claim 1, wherein the optimizer performs an initial optimization as a fluence-based optimization.

4. The system according to claim 1, wherein the optimizer performs an initial optimization as an aperture-based optimization.

5. The system according to claim 1, wherein generating the dose gradient maps includes generating dose gradients for a single beam of a plurality of beams in the beam's eye view.

6. The system according to claim 1, wherein the optimizer specifies new dose gradients by:

delineating a plurality of beamlets of a beam in the beam's eye view; and specifying required dose gradient levels for delineated regions.

7. The system according to claim 1, wherein the display displays the dose distributions, the dose gradient maps, and the dose gradients in relation to a tumor or an organ at risk to the user in real time.

8. The system according to claim 1, wherein the user interface accepts user input to manipulate optimizations.

9. A non-transitory computer readable medium carrying software for controlling one or more processors to perform a method for optimizing an intensity modulated radiation therapy plan, the method comprising:

optimizing the intensity modulated radiation therapy plan with an optimizer according to initial plan specified settings to create optimized dose distributions in a beam's eye view;

generating dose gradient maps from the optimized dose distributions in the beam's eye view;

receiving specified dose gradients and specified sub-regions;

specifying new dose gradient maps for user specified regions in the beam's eye view wherein the specifying includes generating the new dose gradient maps from the received specified dose gradients and the specified sub-regions; and controlling a display to display the new dose gradient maps.

10. The non-transitory computer readable medium according to claim 9, further including:

performing a second optimization using the specified dose gradients.

11. The non-transitory computer readable medium according to claim 9, wherein an initial optimization is a fluence based optimization.

12. The non-transitory computer readable medium according to claim 9, wherein an initial optimization is an aperture based optimization.

13. The non-transitory computer readable medium according to claim 9, wherein each generated dose gradient map shows the dose gradients for a single beam of a plurality of beams in the beam's eye view.

14. The non-transitory computer readable medium according to claim 9, wherein the step of specifying new dose gradient maps includes:

delineating a plurality of beamlets of a beam in the beam's eye view; and specifying dose gradient levels for delineated regions.

15. The non-transitory computer readable medium according to claim 9, including:

controlling the display to display the dose distributions and the dose gradient maps in relation to a tumor or organ at risk for user review on the display.

16. The non-transitory computer readable medium according to claim 15, wherein the user manipulates the dose gradients through a user input.

17. An intensity modulated radiation therapy treatment plan optimization system including one or more processors programmed to:

optimize an intensity modulated radiation therapy plan according to initial plan specified settings to create optimized dose distributions for a beam's eye view;

divide the dose distributions into a plurality of beamlets;

calculate a first dose gradient value for each beamlet of the plurality of beamlets;

compile dose gradient maps from the dose gradient value of each beamlet;

receive user input from a user interface indicating insufficient dose gradients within dose gradient maps of each beam's eye view;

receive user input from a user interface of delineated sub-regions within the dose gradient maps with respect to the insufficient dose gradients;

receive user input from a user interface of user-specified dose gradients for the delineated sub-regions; and perform a second optimization using the user-specified dose gradients.

18. The system according to claim 17, wherein performing the second optimization includes:

applying a limiting factor to an objective function such that a first dose gradient is limited by an optimizer only when the first dose gradient exceeds a user dose gradient for a specific beamlet.

19. The system according to claim 17, wherein an optimizer performs the second optimization.

* * * * *